United States Patent [19]
Isozaki

[11] Patent Number: 6,108,078
[45] Date of Patent: Aug. 22, 2000

[54] METHOD AND APPARATUS FOR SURFACE INSPECTION

[75] Inventor: Hisashi Isozaki, Tokyo, Japan

[73] Assignee: Kabushiki Kaisha Topcon, Tokyo, Japan

[21] Appl. No.: 09/196,739

[22] Filed: Nov. 20, 1998

[30]   Foreign Application Priority Data

Nov. 21, 1997 [JP] Japan .................................... 9-336566
Nov. 21, 1997 [JP] Japan .................................... 9-336572

[51] Int. Cl.$^7$ ................................................. G01N 21/00
[52] U.S. Cl. ..................................... 356/237.2; 356/237.4
[58] Field of Search ............................. 356/237.1, 237.2,
356/237.3, 237.4, 237.5, 445, 446, 338,
239.7, 239.8; 250/559.4, 559.45

[56]   References Cited

U.S. PATENT DOCUMENTS

| | | | |
|---|---|---|---|
| 4,162,126 | 7/1979 | Nakagawa et al. | 356/237.2 |
| 4,410,278 | 10/1983 | Makihira et al. | 356/445 |
| 4,508,450 | 4/1985 | Ohshima et al. | 356/237.2 |
| 4,902,131 | 2/1990 | Yamazaki et al. | 356/237.2 |
| 5,293,538 | 3/1994 | Iwata et al. | 356/239.1 |
| 5,602,646 | 2/1997 | Bernardin et al. | 356/237.2 |

*Primary Examiner*—Hoa Q. Pham
*Attorney, Agent, or Firm*—Foley & Lardner

[57]   ABSTRACT

A foreign matter on the surface of an object of inspection is detected by throwing an inspecting light beam on the surface of the object of inspection and sensing a scattered light beam reflected from the surface of the object of inspection while the inspecting light beam is allowed to make a spiral scan. When the signal of the scattered light beam by the foreign matter exceeds a threshold signal at a point while the inspection light beam scans the object in the predetermined direction, the point is stored as a start point and, when, thereafter, the foreign-matter scattered signal falls below the threshold signal at a point, the point is stored as an end point, and, further, a point between the start point and the end point where the foreign-matter scattered signal was at its maximum level is stored as a peak. A threshold signal level is established between the effective range where a foreign matter or flaw is measured and the circumferential range beyond the effective range. While measurement is being made in the effective range, when the threshold signal level is exceeded at a point, the point is set as a start position and, when the threshold signal level is exceeded thereafter, the point is set as an and position. The manner of measurement between the start position and the end position is made different from the manner of measurement in the effective range and, further, the manner of measurement between the start position and the end position and the manner of measurement in the effective range are automatically charged over.

19 Claims, 19 Drawing Sheets

PIXELS JUDGED CONTINUOUS BECAUSE OF
BEING CONTIGUOUS TO EACH OTHER

INDICATES PIXEL; COLORED PIXELS INDICATE CONTOUR

EFFECTIVE RANGE

CIRCUMFERENTIAL RANGE

EFFECTIVE RANGE

CIRCUMFERENTIAL RANGE

METHOD AND APPARATUS FOR SURFACE INSPECTION

FIELD OF THE INVENTION

The present invention relates to a method of surface inspection for inspecting a foreign matter ("foreign matter" herein is a comprehensive term embracing a dust, flaw, and the like) present on the surface of an object of inspection such as a wafer and an apparatus for carrying out the method.

PRIOR ART

Such a method for surface inspection has so far been known in which a light beam from a light source is thrown on the surface of an object of measurement through an optical system and a scattered light beam reflected from the surface of the object of measurement is sensed by a photoelectric converting element, while the object of measurement and the optical system are provided with relative displacement, whereby a foreign matter on the surface of the object of measurement is inspected and the position coordinates of the foreign matter are recorded. As the converting element, a photomultiplier for example is in use.

An object of measurement such as a wafer has an effective range of measurement. Foreign matter/flaw is inspected within the effective range.

A photomultiplier having a high sensitivity is quite capable of measuring a scattered light beam from a foreign matter on the wafer. However, the region outside the effective range, i.e., a circumferential range, is frequently dirty. Therefore, a great amount of scattered light is generated in the circumferential range, not to be compared with that in the effective range. Because the circumferential range has an edge portion of the wafer, an extremely great amount of scattered light is produced there.

However, conventional apparatuses for foreign matter inspection measure the circumferential range and the effective range on the basis of the signal from the same photomultiplier. Therefore, when a great amount of scattered light is produced in the circumferential range, a saturation phenomena due to the characteristic of a photomultiplier occurs. Because of this, it sometimes becomes impossible for such an apparatus to continue the measurement for a certain period of time.

For example, such a state in which the measurement becomes impossible is shown in FIG. 17. A light beam from a light source is thrown on the surface of an object of measurement through an optical system and a scattered light beam reflected from the surface of the object of measurement is sensed by a photoelectric converting element, while the object of measurement and the optical system are provided with relative displacement, and a scanning light beam is continuously directed to a plurality of objects of measurement, whereby a foreign matter on the surface of the object of measurement is inspected. While the effective range is inspected, there arises no problem. However when the scanning light beam enters the circumferential range of the wafer, i.e., enters the circumferential range beyond the effective range, a great amount of scattered light is produced as shown at the bottom of FIG. 3 and, thereby, the photomultiplier is put into the saturated state and it is made impossible to perform the measurement for a certain period of time thereafter. This state is shown, as the photomultiplier dead zone in FIG. 17.

Since there is the above described problem arising from the principle of the photomultiplier, it has been unavoidable in the conventional method of surface inspection with the use of a photomultiplier that the dead zone is produced by the effect of the strong scattered light beam from the edge portion of the wafer. Especially when there is present a U or V notch or the like in the wafer, accurate surface inspection becomes difficult. In fact, accurate measurement of the edge is impossible.

Let it be supposed, while the conventional method for surface inspection with the use of a photomultiplier as shown in FIG. 17 is used, that another sensor is also used for inspecting the surface of the wafer. Then, even if measurement data of the wafer surface are stored, the processing may become useless as shown in FIG. 18 when position coordinates are not accurate or they are not recorded at all, Therefore, various forms of data processing are being performed on the measurement data in the circumferential range.

Whichever data processing method may be used, it is difficult, from principle, to perform accurate measurement. As for the measurement of the coordinates in the circumferential range, no accurate measurement method has yet been established.

Even if another sensor is used only for measurement of the circumferential range, the measurement and data processing may have to be made separately from that of the sensor used for measurement in the effective range. Thus, it is theoretically impossible to accurately match the position coordinates obtained by both the sensors.

Such a method may be considered as to employ another low-sensitivity sensor for sensing reflected light by regular reflection of an inspecting light beam and subject the obtained data to the same processing as that for foreign matter inspection, to thereby accurately measure the circumferential range. However, even if the data in the circumferential range are accurately measured by the employment of another sensor sensing the reflected light by regular reflection of the inspecting light beam, the quantity of the pertinent coordinate data will become too huge to be processed in the same way as in the processing of the foreign matter data and a large volume of memory will become necessary. This follows a serious problem of cost increase for processing data and constructing hardware.

When pixel processing is made without having coordinate data, since coordinate data are absent even if data are present, it is impossible to obtain accurate measurement data in the circumferential range.

Such a method and apparatus for surface inspection, in which an inspecting light beam is thrown on the surface of an object of inspection through an optical system, a scattered light beam reflected from the surface of the object of inspection is sensed, the object of inspection and the optical system are provided with relative displacement in the meantime such that the inspecting light beam makes a spiral scan, and thereby a foreign matter on the surface of the object of inspection is inspected, is known. In such a conventional method and apparatus for surface inspection on the spiral scan system, the detection of the foreign matter signal is performed by making sampling along the scanning direction of the inspecting light beam at each of divided sections at predetermined intervals (divided for example by an encoder signal) and by detecting the largest signal therein and recording only such data. The method to store only the maximum data in each of the divided sections is called "pixel system".

FIG. 2 shows a processing method on a conventional pixel system. In the section A, the data Da takes on the maximum value. In the section B, the data Db takes on the maximum value. According to a known software processing method on the pixel system, it is determined that there is one foreign matter or there are two foreign matters in this case. For example, in the case where they are judged to be continuous by software, the number becomes one. In the case where they are judged discontinuous, the number becomes two.

FIG. 7 shows a method on another conventional pixel system of surface inspection, in terms of determination of the existence of continuity.

The determination in the scanning direction in FIG. 7 is made as follows. Namely, in the section A, the data Da takes on the maximum value and, in the section B, the data Db takes on the maximum value. Depending on the software processing method on the pixel system, the number of the foreign matters becomes one or two. In the case of software judging them to be continuous, the number becomes one. In the case of software judging them to be discontinuous, the number becomes two.

In the state of inspection shown in FIG. 7, determination of the existence of continuity in the direction of feed indicated by the arrow is made as shown In FIG. 8. The portion shown black is that judged to be continuous because pixels are contiguous to each other.

In the pixel system, processing is made on a one-foreign-matter-in-one-section basis. Therefore, in the judgment as to a foreign matter astride the boundary line, the processing is made only depending on information of pixels adjoining each other, without having any data indicating existence of a continuity therein.

In processing data in the direction of feed, information of points is developed into a pixel image and judgment is made on the basis of information of adjacency, the same as in the direction of scan.

Further, in a method for surface inspection making a constant scan with the use of a galvano-mirror or the like, the sampling frequency is mutually related with the scanning speed and the size of the bundle of rays and all the signals that exceed a threshold signal are stored and treated as data of points. Such a system is called "scan system".

In the scan system, the number of data becomes larger and the memory capacity increases as the sampling frequency is made higher. Therefore, the sampling frequency is set low and each piece of data is taken at intervals of several tens of micrometers of the traveling of the scanning light beam. Accordingly, the determination of the existence of continuity largely depends on the traveling speed of the detecting light beam and the sampling frequency. Namely, the data sampled at intervals of a low sampling frequency are regarded as a collection of points and the determination of the existence of continuity is made by software.

In the prior art on either system (of the pixel system and the scan system), the determination of the existence of continuity is made depending on uncertain data.

Since, in either of the pixel system and the scan system, the determination of the existence of continuity has been made while there are absent the very data directly indicating a continuity, it has been impossible to detect a foreign matter correctly and certainly when the foreign matter is in the form of a lump or there are small foreign matters isolated from each other.

As for the direction of feed, the determination of the existence of continuity has been made without having any relevant information.

SUMMARY OF THE INVENTION

An object of the invention is to provide a method and apparatus for surface inspection enabled to detect a foreign matter in the form of a lump or small foreign matters isolated from each other without increasing the memory capacity by having data of continuity through making sampling at a high frequency.

Another object of the invention is to provide a method and apparatus for surface inspection capable of determining the existence of continuity in the direction of feed by using data with continuity in the direction of scan and judging that the data are overlapping with each other with respect to the direction of feed on the basis of positional information.

A further object of the invention is to provide a method and apparatus for surface inspection capable of suitably detecting foreign matters and the like on a wafer, even in the circumferential range beyond the effective range.

According to an aspect of the invention, in a method of surface inspection for inspecting a foreign matter on the surface of an object of inspection by throwing an inspecting light beam on the surface of the object of inspection through an optical system and sensing a scattered light beam reflected from the surface of the object of inspection, while the object of inspection and the optical system are provided with relative displacement, the method of surface inspection comprises the steps of storing the point where the scattered light signal by a foreign matter exceeds a threshold signal while the inspecting light beam is scanned in a predetermined direction as a start point, storing the point where the foreign-matter scattered signal thereafter falls below the threshold signal as an end point, and storing the point where the foreign-matter scattered signal was at its maximum level between the start point and the end point as a peak.

Preferably, in the method, a foreign matter on the surface of an object of inspection is inspected on the basis of positional information, as position data of the foreign-matter scattered signal, including at least a start point, a peak, and an end point. The direction of scan of the inspecting light beam is composed of the scan direction and the feed direction and it is judged that there is continuity in the foreign-matter scattered signal with respect to the feed direction when the positional information including the start point and the end point of a piece of data is overlapping with another piece of data in the feed direction. The stretch from the start point to the end point is considered to be a continuous foreign matter and a process to detect the peak data is constantly performed between the start point and the end point. An end point is stored at the point of time at which a piece of data has fallen for the first time below the threshold signal, counting of the sampling clock is started at the time of point of the end point, and, when the data has risen above the threshold signal again within preset data (which is variable), the earlier stored end point is cleared and the process for detecting peak data is continued further.

The method and apparatus for surface inspection of the invention produces its best effect when a semiconductor wafer is used as the object of inspection. Especially when a foreign matter on the surface of the object of inspection is so large as to be astride the lines of scan, the determination of the existence of continuity can be made accurately. For example, continuity along the line of scan can be accurately detected. Moreover, a foreign matter astride the lines of scan (perpendicularly extended thereto) can be detected as a continuous one.

The method and apparatus for surface inspection according to the invention is such that throws an inspecting light beam on the surface of an object of inspection and senses a scattered light beam reflected from the surface of the object of inspection, while the inspecting light beam in scanned for example in a spiral manner, so that a foreign matter on the surface of the object of inspection is inspected, and, when the foreign-matter scattered signal exceeds a threshold signal while the inspecting light beam is scanned in the predetermined direction, stores the point as a start point and, when thereafter the foreign-matter scattered signal falls below the threshold signal, stores the point as an end point, and, then, stores the point between the start point and the end point where the foreign-matter scattered signal was at its maximum level as a peak. Of such method and apparatus, preferred forms of main components of the present invention will be described below.

The data of a start point is the data of the address of the point of time at which the scattered signal level exceeds a threshold signal.

The data of a peak is the data of the signal at its maximum level at a point between a start point and an end point and the address of the point.

The data of an end point is the data of the address of the point of time at which the signal falls below the threshold signal level, after passing the peak point, to which, however, a condition is attached as described later.

Preferred data detecting procedure is as follows:

(1) A sufficiently fast sampling frequency (for example 20 MHz) is provided for the inspecting light beam in the scanning direction.

(2) When the foreign-matter scattered signal exceeds a threshold signal, the data of the point is stored as the data of a start point.

(3) In succession thereto, peak data processing is made.

(4) When the foreign-matter scattered signal falls below the threshold signal, the data of this point is stored as end-point data E1.

(5) At the same time as the step (4) is executed, counting of the sampling cycles is started, whereby the period of time during which the scattered signal is below the threshold signal is counted.

(6) The number of counts is compared with preset data and when it becomes greater than the data, the processing for setting the end point is completed and the relevant data is transferred to the memory to be stored therein as data of one foreign matter. When the foreign-matter scattered signal exceeds the threshold signal again before the counts for comparison has been counted out, next step follows.

(7) The earlier stored end-point data E1 is cleared and the peak data processing is kept on.

(8) Thereafter, processing of steps (4)–(7) is made.

The data processing method for determination of the existence of continuity is performed as follows:

(1) While processing of determination of the existence of continuity in the scanning direction is made, if the distance from the start point to the end point is found greater than a predetermined value, it is judged that there is a flaw. Otherwise, it is judged that there is a dust.

(2) As to processing in the direction of feed, it is determined whether or not pieces of data, having positional information including a start point and an and point, are overlapping each other. If they are overlapping each other, it is judged that there is a continuity existent in the direction of feed. When the number of pieces of the data continuous in the direction of feed is found greater than a predetermined number, what is present there is judged as a flaw. Otherwise, it is judged as a dust According to another aspect of the invention, there is provided a method for surface inspection, in which a threshold signal level is set up between an effective range in which a foreign matter/flaw is measured and a circumferential range beyond the effective range; when the threshold signal level is exceeded at a point by the foreign-matter scattered signal while the effective range is measured, the position is set as a start position, and, when thereafter the threshold signal level is exceeded at a point, the position is set as an end position, wherein the manner of measurement between these start position and the end position is changed from the manner of measurement in the effective range, and the manner of measurement between the start position and the end position and the manner of measurement in the effective range are automatically changed over.

Preferably, the quantity of reflected light is stored, while measurement for a foreign matter is being made in the effective range, only when existence of a foreign matter is detected, whereas the quantity of reflected light is mainly measured while measurement is being made in the circumferential range and the quantity of reflected light is subjected to a minimum value process. Further, it is preferred that any desired sampling manner can be switch selected and the measurement speed is also variable in each of the effective range and the circumferential range. Especially, in the effective range where a foreign matter or flaw is measured, the maximum values as well as the relevant coordinates, the start position, and the end position of the foreign matter or flaw are measured and, in the region of measurement of the circumferential regions the minimum value, as well as the relevant coordinates, the start position, and the end position in the edge portion of the object of measurement are mainly measured. Further, the data memory has an arbitrary address for common use and the data stored in a memory in conformity with the range of measurement is changed.

In the method for surface inspection of the invention, the effective range where a foreign matter/flaw is measured and the circumferential range beyond the effective range are clearly diutinguished from each other and there is set up a threshold signal level between the effective range and the circumferential range. In the effective range, a foreign matter/flaw is primarily measured. While measurement of a foreign matter/flaw is being made, if the aforesaid threshold signal level is exceeded by the foreign-matter scattered signal, the position is set as a start position. When thereafter the threshold signal level is exceeded, the position is met as an end position. It is an essential point of the invention that the manner of measurement in the region between the thus determined start position and end position and the manner of measurement in the effective range are made different. Moreover, the manner of measurement in the region between the start position and end position and the manner of measurement in the effective range are automatically changed over.

Main data used in the method for surface inspection according to the invention are as follows:

(1) data of the maximum value of a foreign matter;

(2) data of the start position of the foreign matter;

(3) data of the end position of the foreign matter; and (4) data of the quantity of reflected light from the foreign matter.

Main processes performed in the method for surface inspection according to the invention are as follows:

(1) to determine data of measurement positions of the effective range where a foreign matter is inspected and the circumferential range beyond the effective range;

(2) to chiefly measure a foreign matter in the effective range, which is inspected for a foreign matter, and, only when a foreign matter is found present, to store the data of the quantity of reflected light; and (3) to chiefly measure the quantity of reflected light in the circumferential range and to perform, at this time, a minimum value process and record the relevant data, as well as the start position and the end position.

Through measurement of these various data and making processing on these data, the same accuracy of coordinates can be obtained in the circumferential range as obtained in the inspection of a foreign matter. Thus, accurate measurement in the edge portion (circumference) can be achieved.

Further, by having the data in the effective range for inspecting a foreign matter and the data in the circumferential range beyond the effective range commonly stored, the need for use of a large capacity of memory can be eliminated. Consequently, the apparatus can be fabricated at low cost.

DESCRIPTION OF THE PREFERRED EMBODIMENTS

A preferred embodiment of the invention will be described with reference to the accompanying drawings. Embodiment of FIG. 1 and FIGS. 3–5

Figure 1:
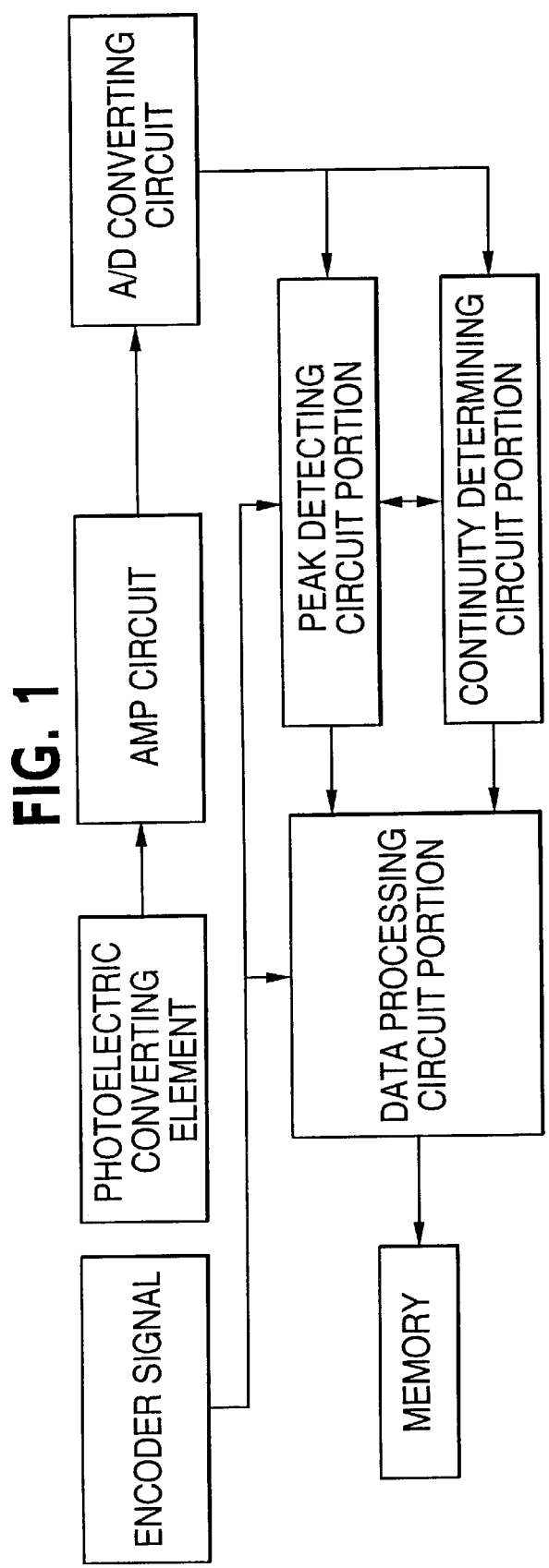
FIG. 1 is a block diagram showing a first embodiment of the invention.
Figure 2:
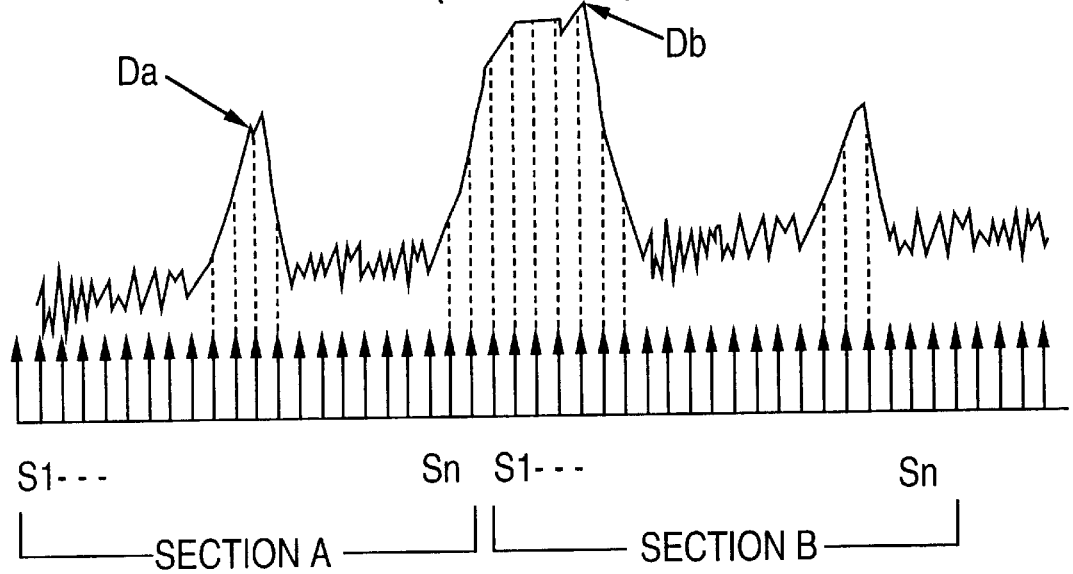
FIG. 2 is a diagram showing a processing method on a prior art pixel system.

FIG. 1 is a block diagram showing an embodiment of the invention.

Referring to FIG. 1, a photoelectric converting element is connected to a peak detecting circuit portion and a continuity determining circuit portion through an AMP circuit and an A/D converter circuit in the order named. The peak detecting circuit portion and the continuity determining circuit portion are connected to a data processing circuit portion. The data processing circuit portion is connected to a memory. An encoder signal is supplied to the peak detecting circuit portion and the data processing circuit portion.

Figure 3:
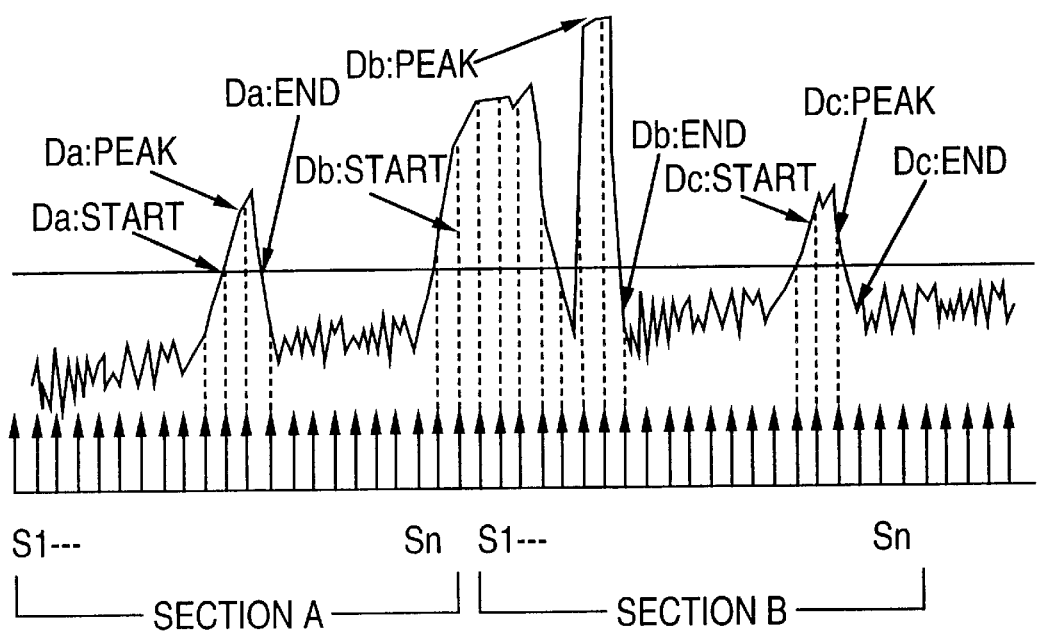
FIG. 3 is a diagram showing the manner of processing in the method of the first embodiment of the invention.

FIG. 3 shows the manner of processing in the method of the invention.

In the method of the invention, while an inspecting light beam is scanned in a predetermined direction, if a foreign-matter scattered signal exceeds a threshold signal (indicated by a horizontal solid line in FIG. 3) at a point, the point is stored as a start point (Start) and, thereafter, if the foreign-matter scattered signal falls below the threshold signal at a point, the point is stored as an and point (End). Further, a point between the start point and the end point where the foreign-matter scattered signal was at its maximum value is stored as a peak (Peak). A foreign matter on the surface of the object of inspection is specified on the basis of positional information, as the position data of the foreign-matter scattered signal, made up of the start point (Start), the peak (Peak), and the end point (End).

In FIG. 3, foreign matters are specified by Da, Db, and Dc and therefore the number of the foreign matters is three. In this ease, the data of the section A and the section B are not related to the number of foreign matters and, hence, the number of foreign matters is counted as three.

Figure 4:
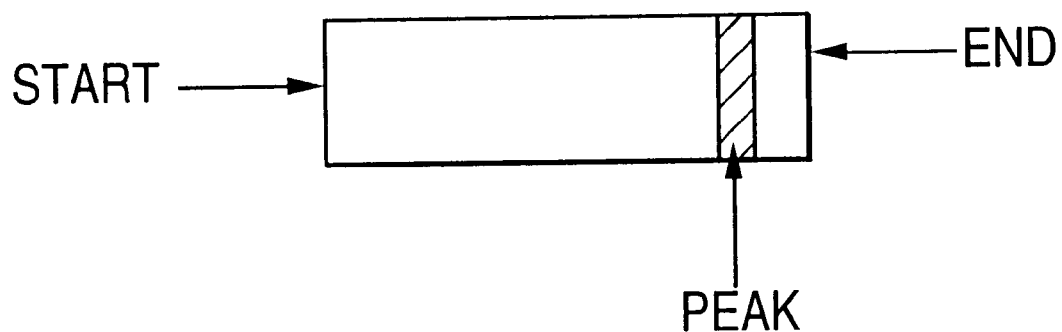
FIG. 4 is a conceptual drawing of determination of the existence of continuity in a foreign matter in the method of FIG. 8.

FIG. 4 shows a concept of judging a met of data as one foreign matter. Taking the foreign matter Db, in particular, the data of the foreign matter Db falls below the threshold signal (indicated by a horizontal solid line in FIG. 3) in the midway as shown in FIG. 4, but because the adjoining segment is near by, it is specified as one foreign matter.

Figure 5:
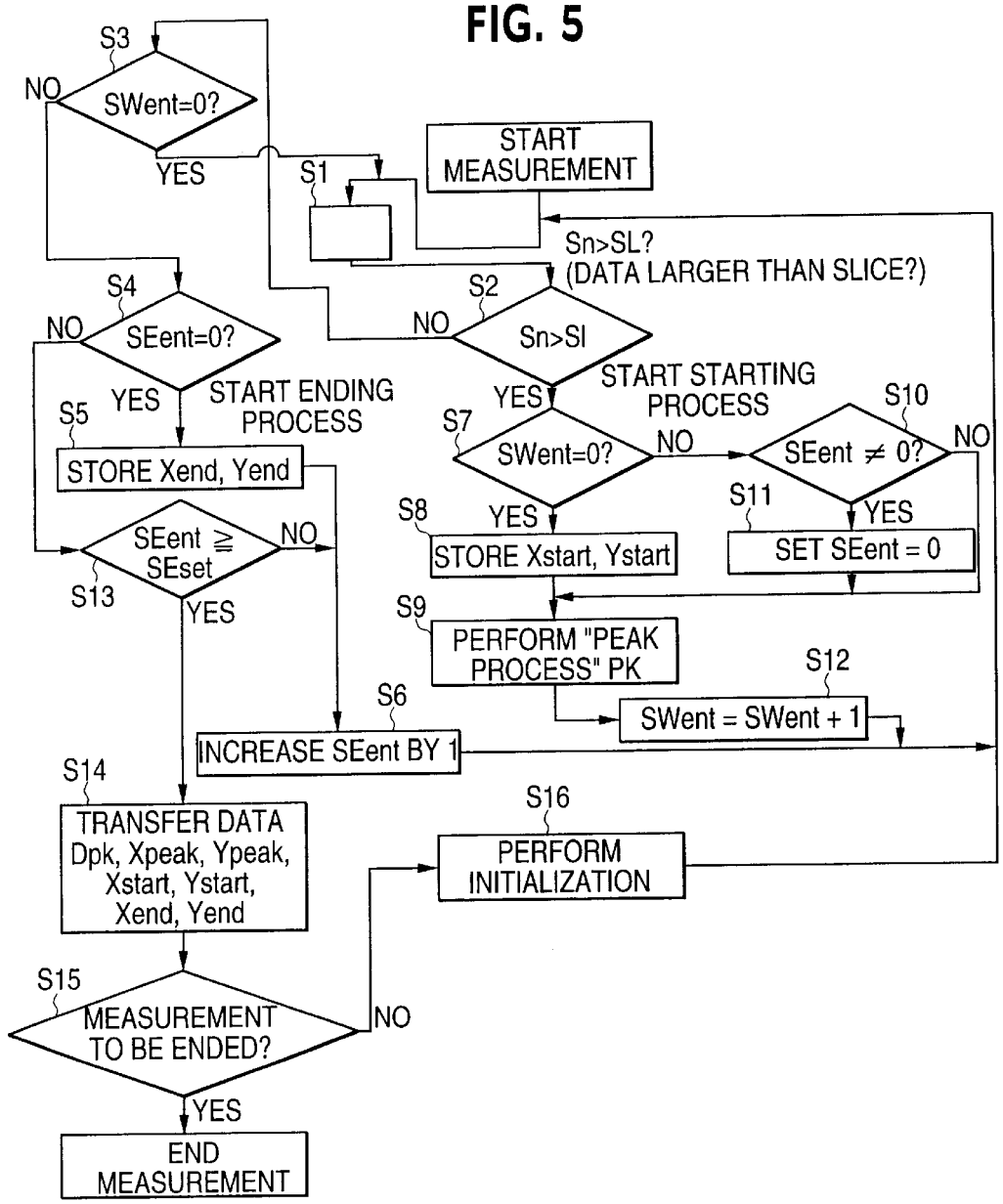
FIG. 5 is a flowchart of the method according to the first embodiment of the invention.

FIG. 5 shows an example of a flowchart of the method according to the invention.

In FIG. 5, first, when the measurement is started, the measured data is input in stop 1 and, then, processing advances to step 2.

In step 2, it is determined whether or not the obtained measurement data Sn is greater than the slice level SL and, when it is smaller than that, processing advances to step 3, whereas, when it is greater than that, it advances to step 7.

In step 3, it is determined whether or not a width count SWcnt, which indicates the width of a foreign matter, is 0, i.e., whether or not the measurement data Sn has already exceeded the slice level SL. In other words, it is determined whether or not the data of a foreign matter was measured immediately before. Here "immediately before" means within the count of a predetermined value SEset, which is determined in step 13.

When the count SWcnt is 0, i.e., when there was no data of a foreign matter immediately before, processing returns to step 1 and, therein, processing of the next measured data is started. When the count SWcnt is not 0, i.e., when there was data of a foreign matter immediately before, processing advances to step 4 and, therein, such a process as to take a count SEcnt (count of non-signal period), i.e., to count the period during which the obtained measurement data Sn is smaller than the slice level SL, is performed.

When SEcnt=0 in step 4, it is determined whether or not an end signal count is 0, and when SEcnt=0, processing advances to step 5. Otherwise, it advances to step 12.

In step 5, namely where the obtained measurement data Sn has lowered from the state of its being above the slice level SL to the state of its being below the slice level SL, the X and Y coordinates at this time are stored as Xend and Yend and processing advances to step 6. In step 8, the SEcnt value is increased by 1 and processing returns to step 1 and, therein, processing of the next measured data is started, When it is determined in step 2 that the obtained measurement data Sn is greater than the slice level SL, processing advances to step 7. In step 7, it is determined whether or not the count of SWcnt is 0, i.e., it is determined whether the measurement data Sn has ever exceeded the slice level SL. When it has just exceeded it for the first time, processing advances to step 8. If it is not for the first time, processing advances to step 10.

In step 8, the coordinate values at this point are stored as the starting coordinates (the coordinates values of the start point) Xstart and Ystart of the foreign matter and then processing advances to step 9.

On the other hand, when it is determined in step 7 that the value of the count SWcnt from the start of a foreign matter is not 0, i.e., that it is not for the first time for the measurement data Sn to have exceeded the slice level SL, processing advances to step 10 and, therein, it is determined whether the count value of the non-signal period count SEcnt is not 0. When the non-signal period count SEcnt is not 0, the count value of the count SEcnt is reset to 0 in step 11 and processing advances to step 9. When the non-signal period count SEcnt is 0, processing directly advances to step 9.

In step 9, peak processing is made to determine whether or not the obtained measurement data at this time is greater than that obtained previously and store the greater of them as the peak data and processing advances to step 12.

In step 12, 1 is added to the value of the count SWcnt from the point of the starting coordinates of the foreign matter (the start point, corresponding to the front edge of the foreign matter) and, then, processing returns to step 1.

When SEcnt≠0, i.e., when the count value of the non-signal period count SEcnt is not equal to 0, processing advances to step 13. It is determined, therein, whether or not the non-signal period count SEcnt is greater than a preset value of the count SEset. When the non-signal period count SEcnt is smaller than the preset value of the count SEset, processing advances to step 6 for processing the next measured data.

On the other hand, when the non-signal period count SEcnt is greater than the preset value of the count SEset, processing advances to step 14 for processing the next measured data.

In stop 14, data of the coordinate values Xstart, Ystart of the start point of the foreign matter stored in step 8, the coordinate values Xend, Yend stored in step 5, and the peak value stored in the memory are transferred to be stored into memory as the coordinate values of the start point, the coordinate values of the end point, and the peak value of the foreign matter under the current inspection and, then, processing advances to step 15.

In step 15, it is determined whether the measurement has been completed. When it is determined that the measurement has been completed, the measurement is ended at this point. If not, processing advances to step 16.

In step 16, initialization is made, i.e., the start coordinate values Xstart, Ystart, the and coordinate values Xend, Yend, and the peak value P of the foreign matter, the non-signal period count SEcnt, and the count value SWcnt from the start of the foreign matter are reset to 0 and processing returns to step 1.

Embodiment of FIG. 6 and FIGS. 8–11

Figure 6:
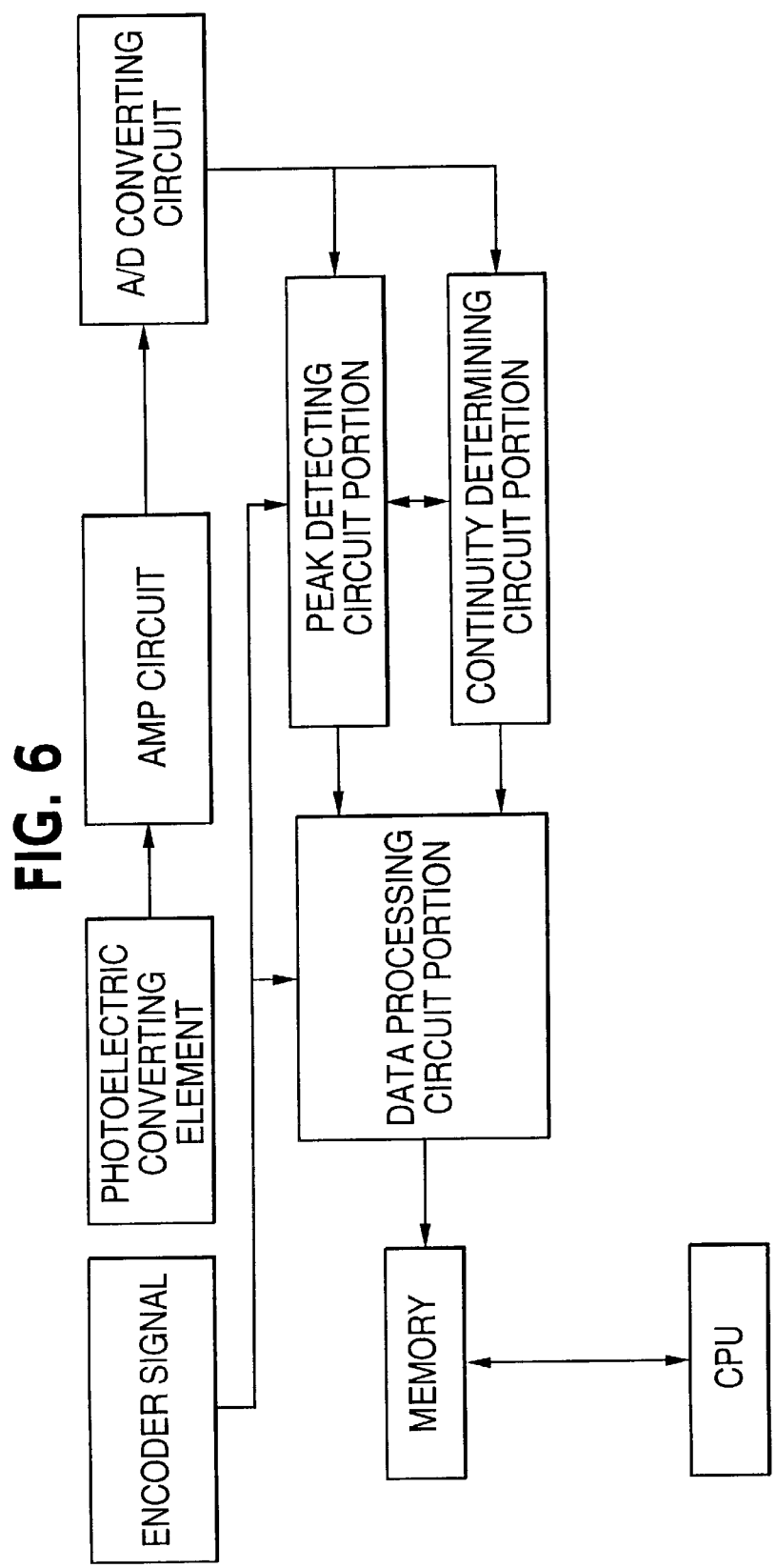
FIG. 6 is a block diagram showing a second embodiment of the invention.
Figure 7:
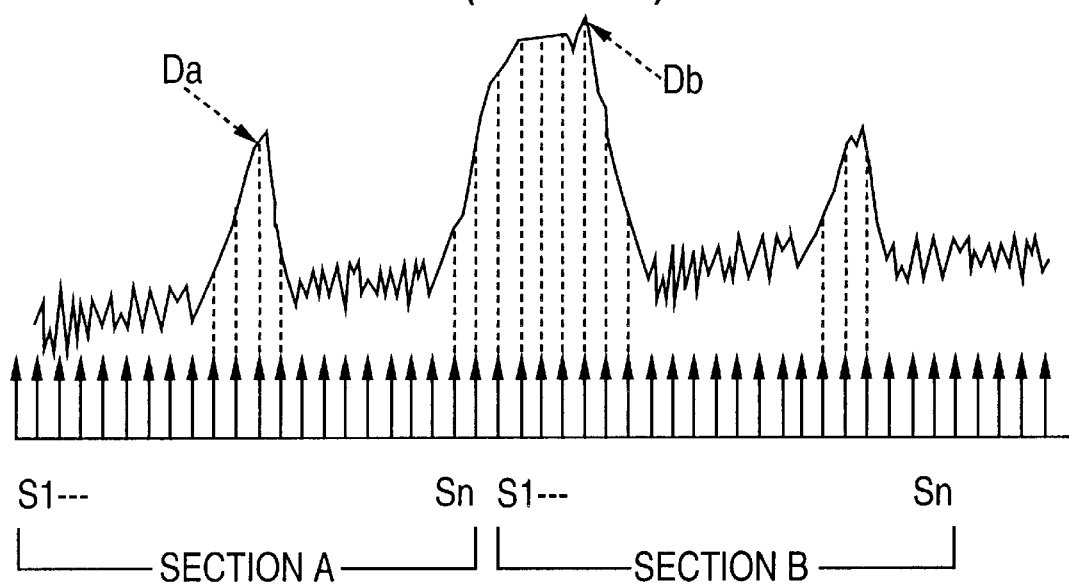
FIG. 7 is a diagram showing a processing method an another prior art pixel system.
Figure 8:
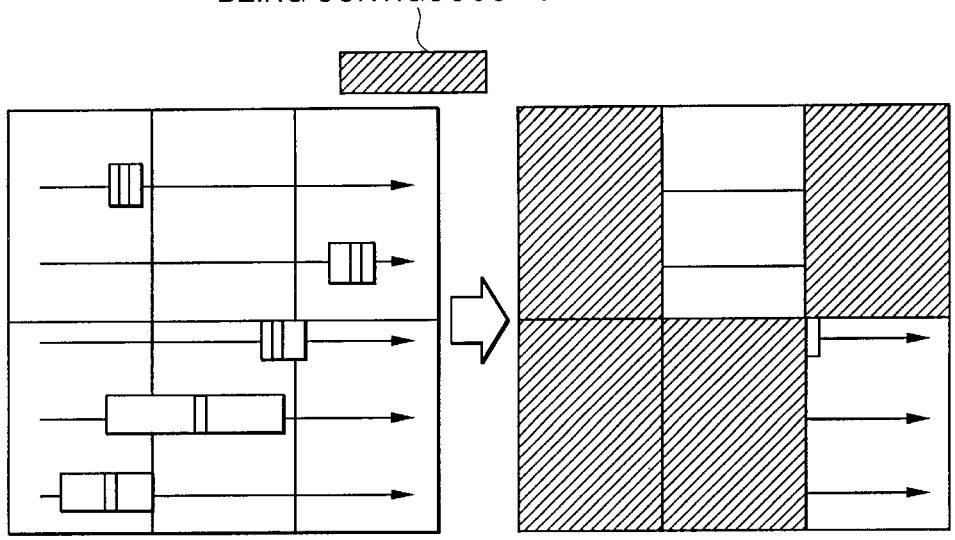
FIG. 8 is a diagram showing the manner to determine the existence of continuity in the direction of feed in the method of FIG. 7.

FIG. 6 is a block diagram showing a second embodiment of the invention.

Referring to FIG. 6, a photoelectric converting element is connected to a peak detecting circuit portion and a continuity determining circuit portion through an AMP circuit and an A/D converter circuit in the order named. The peak detecting circuit portion and the continuity determining circuit portion are connected to a data processing circuit portion. The data processing circuit portion is connected to a memory. An encoder signal is supplied to the peak detecting circuit portion and the data processing circuit portion. Further, a signal from the CPU is supplied to the memory unit.

Figure 9:
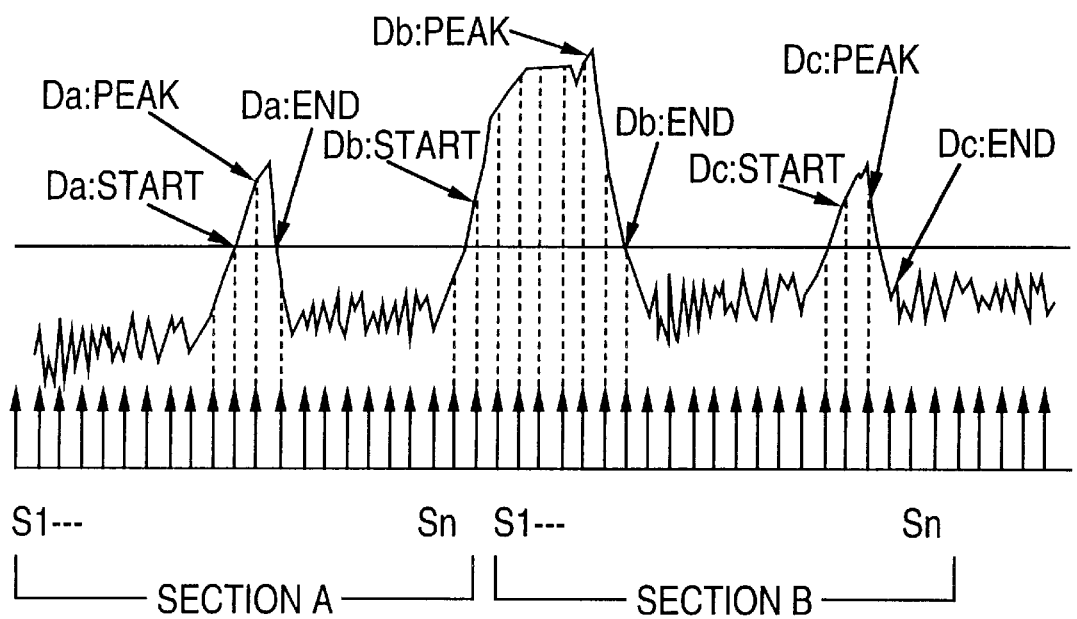
FIG. 9 is a diagram showing the manner of processing in the method of the first embodiment of the invention.

FIG. 9 shows a method of surface inspection according to the second embodiment of the invention.

In the state of inspection shown in FIG. 9, since the data of sections are not related to the number of foreign matters, it is judged that there are three foreign matters Da, Db, and Dc.

This point will further be described below. While an inspecting light beam is scanned in a predetermined direction, when a foreign-matter scattered signal exceeds a threshold signal (indicated by a horizontal solid line in FIG. 9) at a point, the point is stored as a start point (Start) and, thereafter, when the foreign-matter scattered signal falls below the threshold signal at a point, the point is stored as an end point (End). Further, the point between the start point and the end point where the foreign-matter scattered signal was at its maximum value is stored as a peak (Peak). A foreign matter on the surface of the object of inspection is specified on the basis of positional information, as the position data of the foreign-matter scattered signal, made up of the start point (Start), the peak (Peak), and the end point (End). In FIG. 9, foreign matters are specified by Da, Db, An Dc and the number of the foreign matters is three. In this case the data of the section A and the section B are not related to the number of foreign matters and, hence, the number of foreign matters is counted as three.

Figure 10:
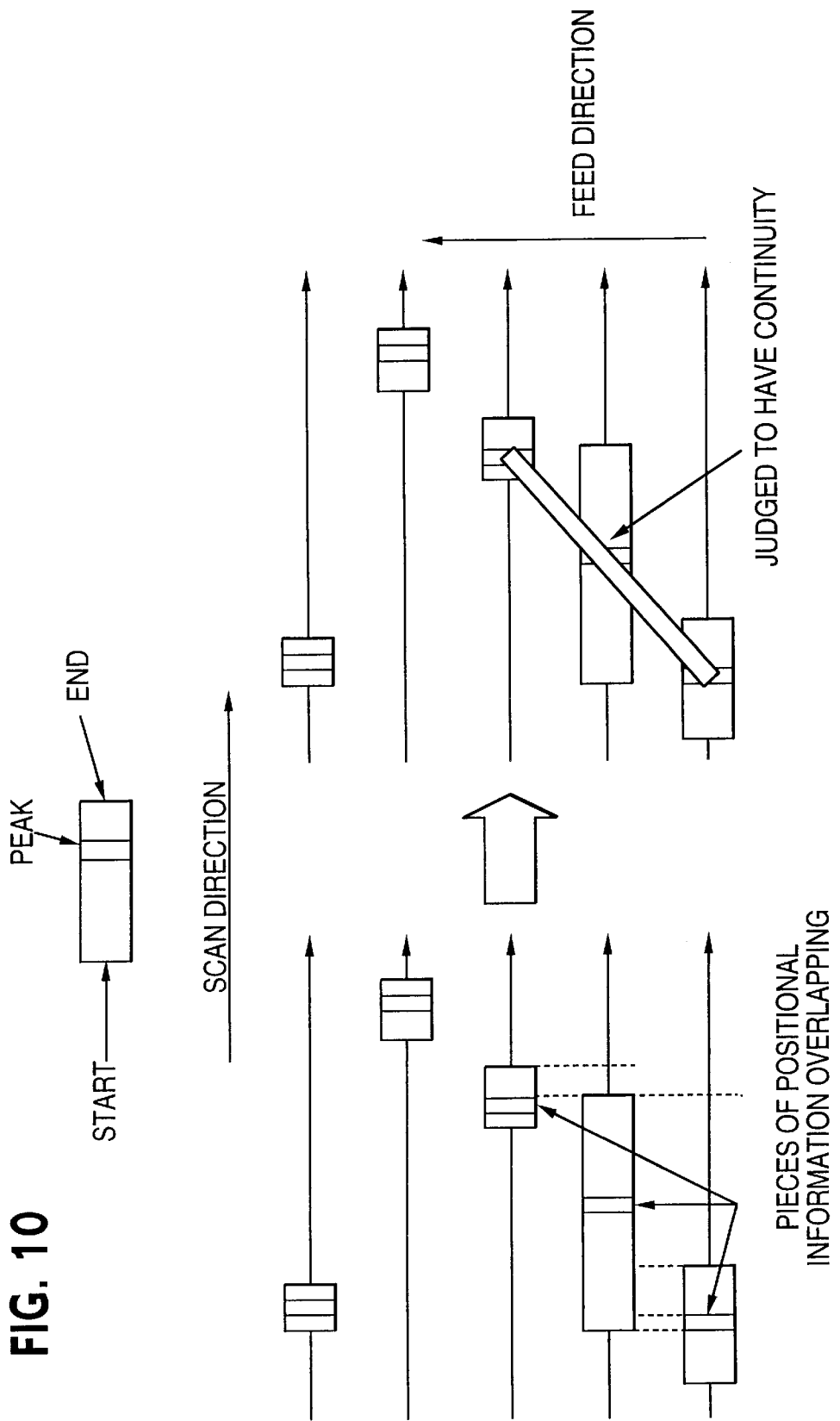
FIG. 10 is a diagram showing the manner to determine the existence of continuity in the direction of feed in the method of FIG. 9.

FIG. 10 is a conceptual diagram as to determination of the existence of continuity in a foreign matter.

In FIG. 10, the direction of the scan made by the inspecting light beam is composed of the direction in which the light beam is scanned and the direction in which the inspected object is fed. When a set of data, each of which is formed of positional information including the start point and as the end point, overlaps each other with respect to the direction of feed, it is determined that the foreign-matter scattered signals have continuity in the direction of feed. The signals from the start point to the end point are judged to represent a continuous foreign matter and the process to detect the peak data between the start point and the end point is constantly performed. At the point where a piece of data has fallen for the first time below the threshold signal, an end point is stored in memory and, at the same time, a sampling clock is started to count. If, then, the data has exceeded the threshold signal again within preset data, the earlier stored end point is cleared and the process for detecting the peak data is continued. Particularly, in processing the data, the following judgments are made as to the continuity.

(1) in the process with respect to the continuity in the direction of scan, if the difference, from the start point to the end point exceeds a predetermined value, the foreign matter is judged as a flaw; otherwise, it is judged as a dust.

(2) As to that in the direction of feed, it is determined whether the data of positional information containing the start point and the end point are overlapping each other. If they are overlapping, it is judged that there is a continuity in the direction of feed. When the number of pieces of the data continuous in the direction of feed exceeds a predetermined number, the foreign matter is judged as a flaw; otherwise, it is judged as a dust.

In the case of FIG. 10, since the two pieces of positional information shown at the top of the drawing are not overlapping each other and hence not continuous, they are judged as two foreign matters. The three pieces of positional information at the bottom of the drawing are overlapping each other and hence continuous, and therefore they are judged to form one foreign matter.

Figure 11:
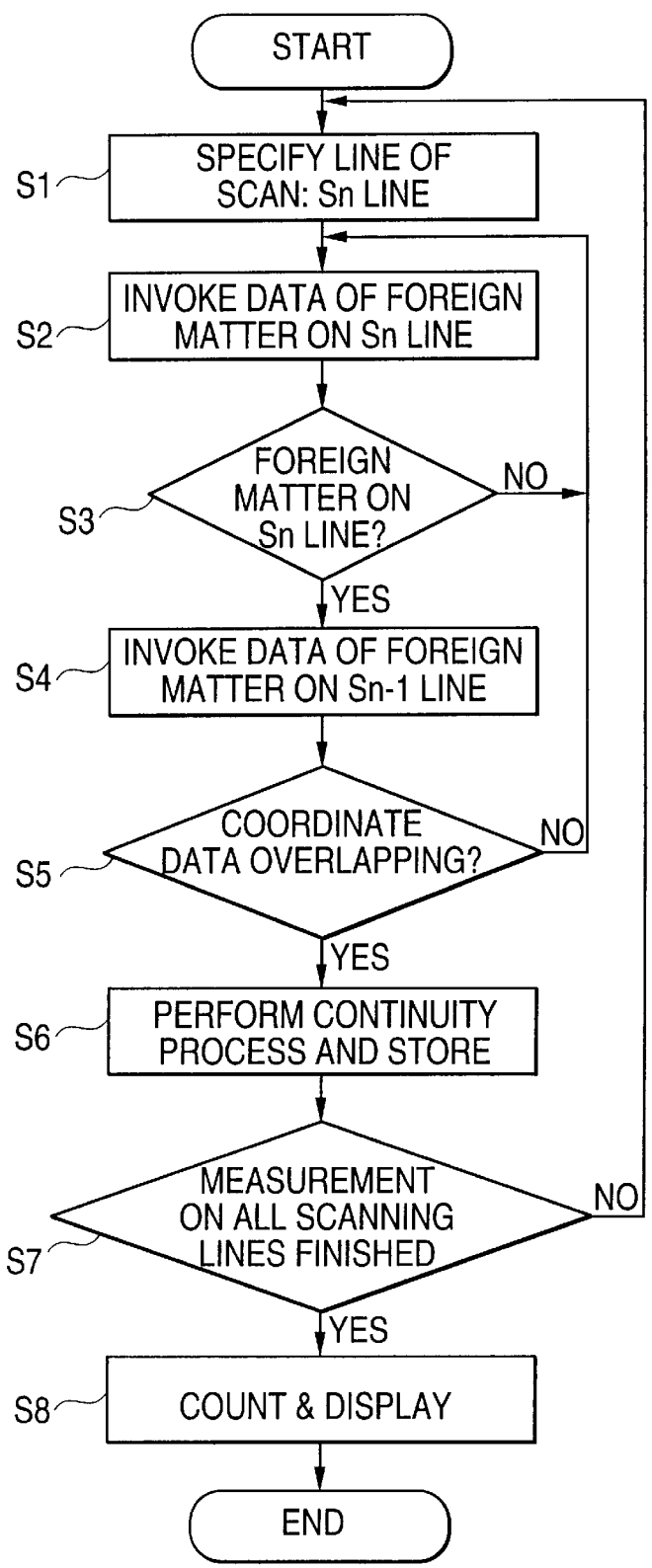
FIG. 11 shows an example of a flowchart of the method according to the first embodiment of the invention.

FIG. 11 shows an example of a flowchart of the method of the invention.

In FIG. 11, when a measurement is started, a line of scan Sn is specified on the object of measurement in step 1 and processing advances to step 2. In step 2, the data on the line of scan Sn of the object of measurement is invoked and processing advances to step 3. In step 3, it is determined whether or not there is foreign matter data on the line of scan, i.e., whether or not there is included a signal exceeding the slice level SL. When there is foreign matter data, processing advances to step 4, and if there is no foreign matter data, processing returns to stop 2 and the pertinent operations are repeated until foreign matter data is detected. In step 4, when foreign matter data is found on the line of scan Sn of the object of measurement, the foreign matter data on the preceding line of scan Sn−1 is invoked and then processing advances to step 6.

In step 5, it is determined whether or not there is an overlap between the foreign matter data on the current line of scan Sn of the object of measurement and the foreign matter data on the preceding line of scan Sn−1 of the object. If there is an overlap between them, processing advances to step 6 and, if there is no overlap, processing returns to step 2.

Here, an example where there is an overlap is such a state in which the stretch from the start coordinate to the end coordinate of a piece of foreign matter data in the direction of scan overlaps with that of another piece of foreign matter data. In step 6, the continuity process is performed and then processing advances to step 7.

When there is present an overlap between the foreign matter data on the current line of scan Sn of the object of measurement and the foreign matter data on the preceding line of scan Sn−1 of the object, it is judged that both the data are such that measure the same foreign matter and, in counting the number of the foreign matters, they are treated as one unit. Accordingly the continuity process involves various processes to associate both the data with each other. For example, such processes are included therein as to treat the data between which continuity is judged present as one group, as to increment a correction value with 1 every time a continuity is found and subtract the correction value from the total number of the foreign matter signals on each line of scan to thereby obtain the correct number of the foreign matters.

In step 7, it is determined whether or not measurement on all the lines of scan of the abject of measurement is finished and, if it is not finished yet, processing returns to step 1 and measurement of the next line of scan Sn is performed.

When measurement of all the lines of scan of the object of measurement is finished, such processes are performed in step 8 as to count the total number of foreign matters in which those foreign matters judged to have continuity between each other are counted as one unit and to display the foreign matters such that those judged to have continuity are distinguishable on a graphic display and, then, the measurement is ended.

Figure 12:
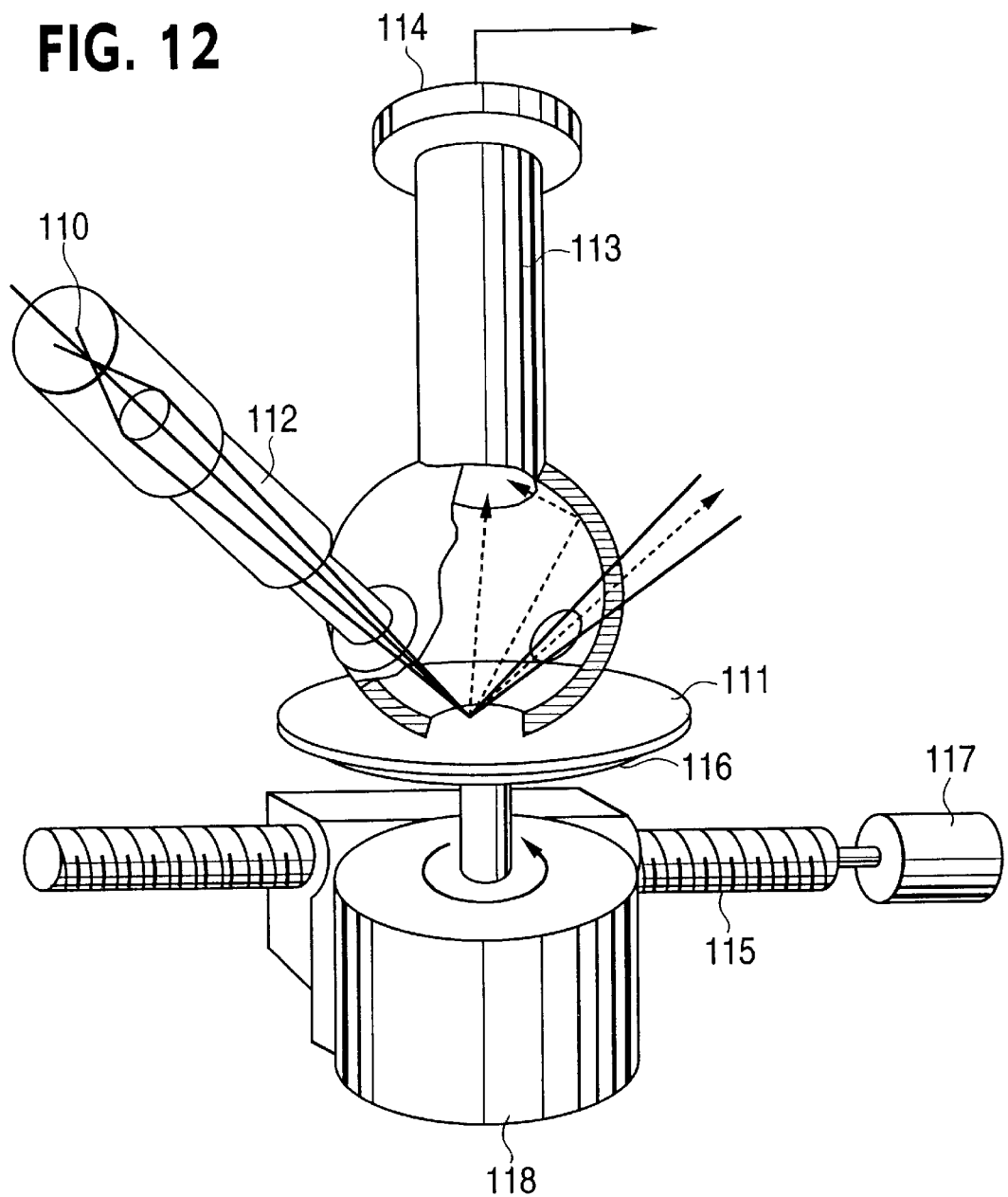
FIG. 12 shows an example of the apparatus for surface inspection according to the invention for carrying out the first and the second embodiments.

Embodiment of FIG. 12

FIG. 12 shows an example of an apparatus for surface inspection on a spiral scan system according to the invention for carrying out the above described two embodiments.

The apparatus comprises a light source 110, an irradiating optical system 112 for throwing a light beam from the light source 110 on the surface of the object of measurement 111, a light receiving optical system 113 receiving a scattered light beam reflected from the surface of the object of measurement 111 irradiated by the irradiating optical system 112 for forming a received-light signal, a photoelectric converting element 114 for outputting the received light by the light receiving optical system 113 as a sensed-light signal, an edge detecting element 120 for receiving a light beam from the light source 110 directed to the circumferential range of the object of measurement, through a recess in the object of measurement, and a linear displacement portion 115 for providing the surface of the object of inspection 111 and the irradiating optical system 112, plus the light receiving system 118, with linear relative displacement, as well as a rotational displacement portion 116 for providing the surface of the object of inspection 111 and the irradiating optical system 112, plus the light receiving system 118, with rotational relative displacement, whereby the irradiating light beam is allowed to make a spiral scan of the surface of the object of inspection 111. The linear displacement portion 115 and the rotational displacement portion 116 are coupled with motors 117 and 118, respectively.

The above described embodiment of the invention can achieve remarkable effects as follows.

(1) Since each piece of the data can be given width and magnitude, an accurate number of foreign matters in conformity with the sampling frequency can be measured.

(2) Processing by software in the direction of scan can be eliminated and, hence, the processing speed can be increased.

(3) By the introduction of the concept of determining the existence of continuity in the established data, problems arising from directivity of scattered light or shapes of foreign matters can be coped with. A decrease in the scattered light beam for a short period of time can be neglected, (4) By having the structure of data overlapping each other with respect to the direction of feed, clear distinction can be made between a continuous flaw and dusts located near by.

(5) Since the data structure indicating the continuity is simple, data measurement can be performed without using a large memory space. Even if an object of measurement has many flaws or a large dust on the surface of it, such a problem can be cleared up that the measurement becomes impossible because of shortage of the memory capacity.

Figure 13:
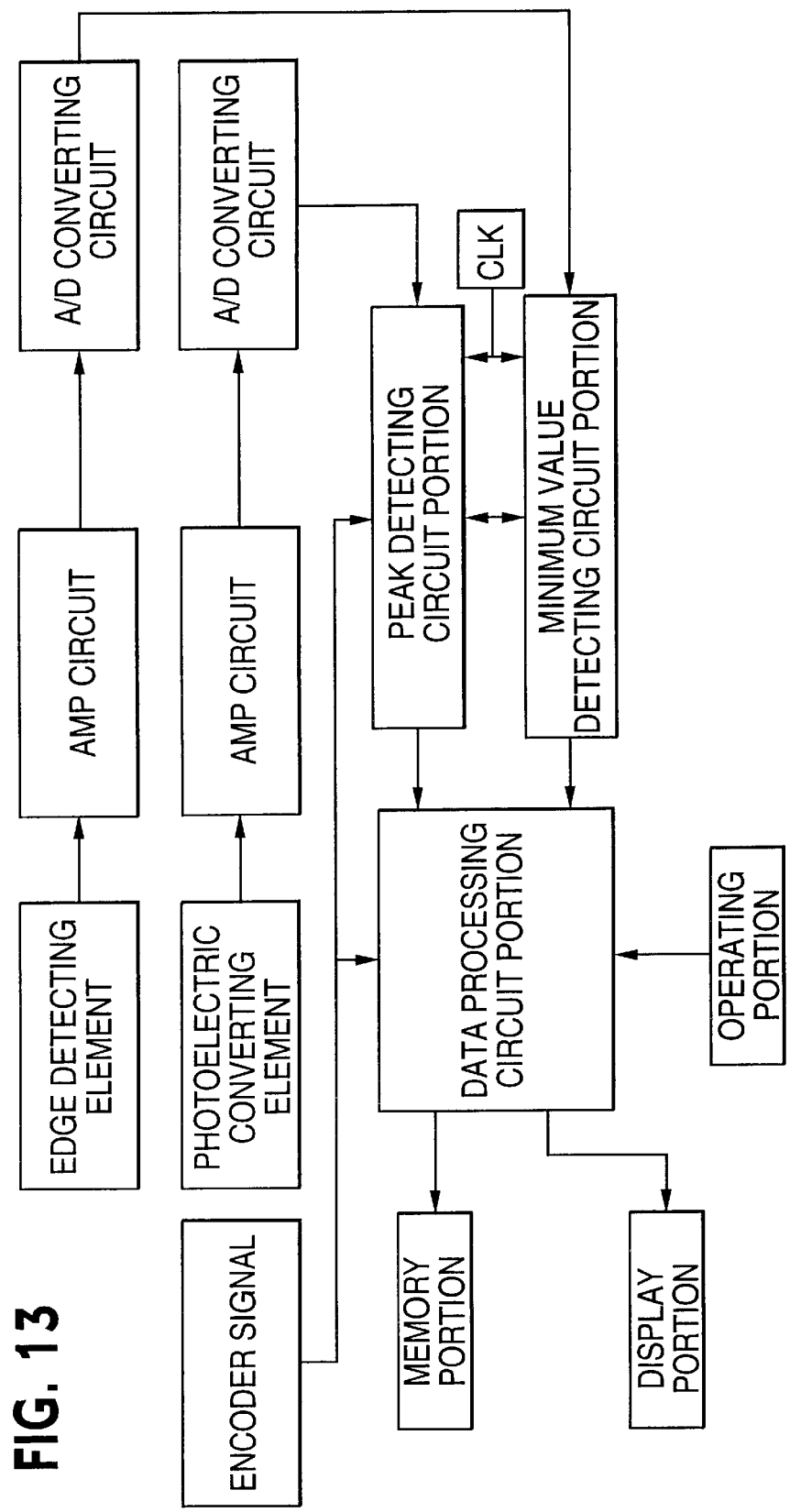
FIG. 13 is a block diagram showing an embodiment of the invention.

FIG. 13 is a block diagram showing another embodiment of the invention.

Referring to FIG. 13, an edge detecting element and a photoelectric converting element are connected, through an AMP circuit and an A/D converting circuit, to a peak detecting circuit portion and a minimum value detection circuit portion, respectively, and both of them are connected to a data processing circuit portion, which, in turn, is connected to a memory portion. An encoder signal is supplied to the data processing circuit portion and the peak detecting circuit portion. Predetermined instructions are given from an operating portion operated by the measuring person.

The apparatus for surface inspection to which the invention is applied is adapted to perform different processes for detecting a foreign matter/flaw in the effective range of an object of measurement and for detecting an orientation flat or a cutting such as a V or U notch in the circumferential range.

As the method of dividing the object of measurement into the effective range and the circumferential range, various methods can be adopted as long as the object of measurement can be unambiguously divided thereby. For example, the ranges may be defined by the measuring person by specifying the coordinate values with the use of the operating portion, namely, by specifying the radius vector r (when the polar coordinate system is employed) or specifying the boundary between the ranges to be some millimeters inward from the circumference.

As another example, a position detecting sensor for detecting relative position between the irradiating optical system, or the photosensing optical system, and the object may be provided so that the division is made according to the output detected thereby.

Figure 19A:
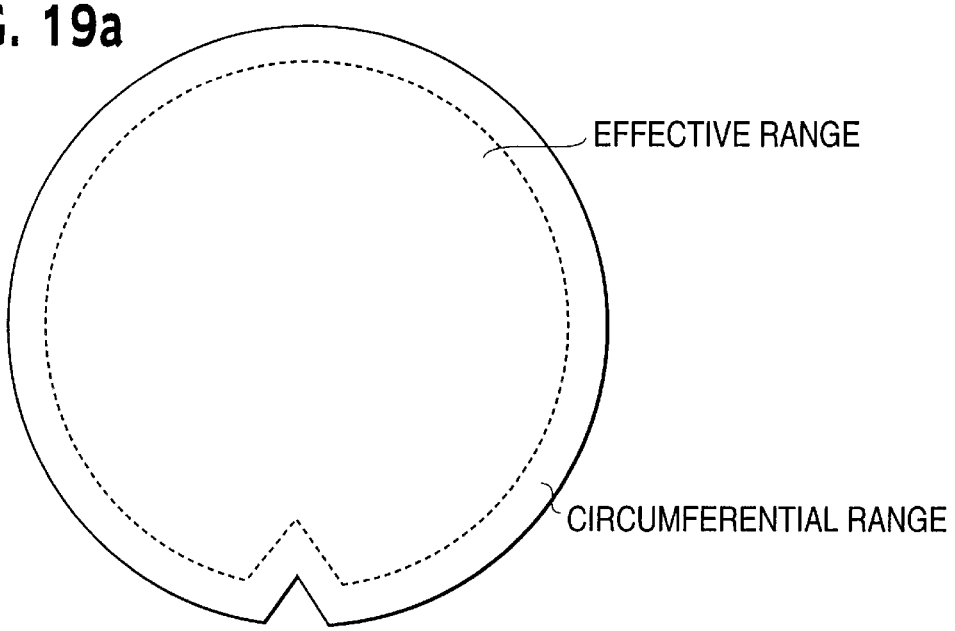
FIG. 19(a) and FIG. 19(b) are diagrams showing distinction made between the effective range and the circumferential range of an object of measurement.
Figure 19B:
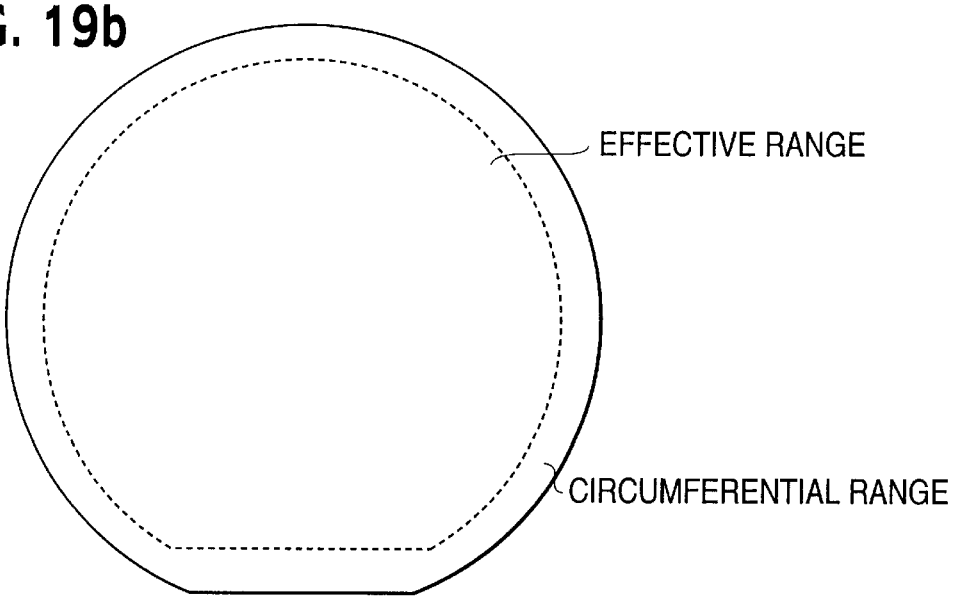

An example of division where a wafer having a notch is used as the object of measurement is shown in FIG. 19(a) and an example of division where a wafer having an orientation flat is used as the object of measurement is shown in FIG. 19(b).

When the apparatus is applied to the inspection of a semiconductor wafer, for example, the object of measurement is a wafer and detection of a foreign matter/flaw is performed in the effective range and a cutting such as an orientation flat is detected in the circumferential range.

First, the case of measurement performed in the effective range of an object of measurement will be described.

In the effective range of the object of measurement, the apparatus for surface inspection measures a foreign matter on the object of measurement by having a light beam from a light source thrown on the surface of the object of measurement through its irradiating optical system and having a scattered light beam from the surface of the object of measurement sensed by its photoelectric converting element, while the object of measurement and the irradiating optical system, plus the photosensitive optical system, are provided with relative displacement so that the light beam continuously scan a plurality of objects of measurement in the arrowed direction. It is preferred that the photoelectric converting element 114 is formed of a photomultiplier in view of its high sensitivity.

An example of sensed-light signals including scattered light beams from foreign matters obtained by the photoelectric converting element in the above described manner is shown in FIG. 3.

The peak detecting circuit portion, when it, during the course of the scan, detects that a scattered-light signal from a foreign matter exceeds the slice level at a point of time according to the signal from the photoelectric converting element, sets this point as a start position and outputs ENm start data according to the signal from the encoder, Ym start data according to the displacement of the linear displacement portion 115, and Xm start data according to the clock signal from the clock circuit CLK as the coordinate data of the point.

When, thereafter, the foreign matter-scattered signal falls below the slice level at a point, the peak detecting circuit portion sets the point as an end position and outputs ENm end data according to the signal from the encoder, Ym end data according to the displacement of the linear displacement portion 115, and Xm end data according to the clock signal from the clock circuit CLK as the coordinate data of the point.

The peak detecting circuit portion sets the point between the start position and the end position where the foreign matter-scattered light signal was at its maximum as the peak and outputs, as the coordinates of the peak and the value of the peak level, ENm data according to the signal from the encoder, Ym data according to the displacement of the linear displacement portion 115, Xm data according to the clock signal from the clock circuit CLK, and the peak level Dm peak.

Here, ENm data is the output of the encoder, of which 6000 pulses, for example, are output for one rotation and indicates a coarse position in the circular direction. Ym data indicates the displacement provided by the linear displacement portion 115, namely the position in the radial direction. Xm data indicates a precise position in the circular direction according to the clock signal from the clock circuit CLK.

Then, the measurement in the circumferential range is performed as described below When it is judged, according to the quantity of the displacement given by the linear displacement portion, that the measurement is being made inside the circumferential range coming over the effective range, the measurement is then made, not with the use of the sensed-light signal from the photoelectric converting element, but with the use of an output signal of the edge detecting element.

Here, the sensitivity of the edge detecting element is set at such a level that is able to make distinction between the light beam reflected from the object of measurement, of the irradiating light beam from the irradiating optical system, and the light beam that is input thereto at the time when the irradiating light beam from the irradiating optical system has stopped reflecting from the object of measurement because of there being an orientation flat or the like. Therefore, the sensitivity of the photoelectric converting element is set higher than the sensitivity of the edge detecting element.

Figure 14:
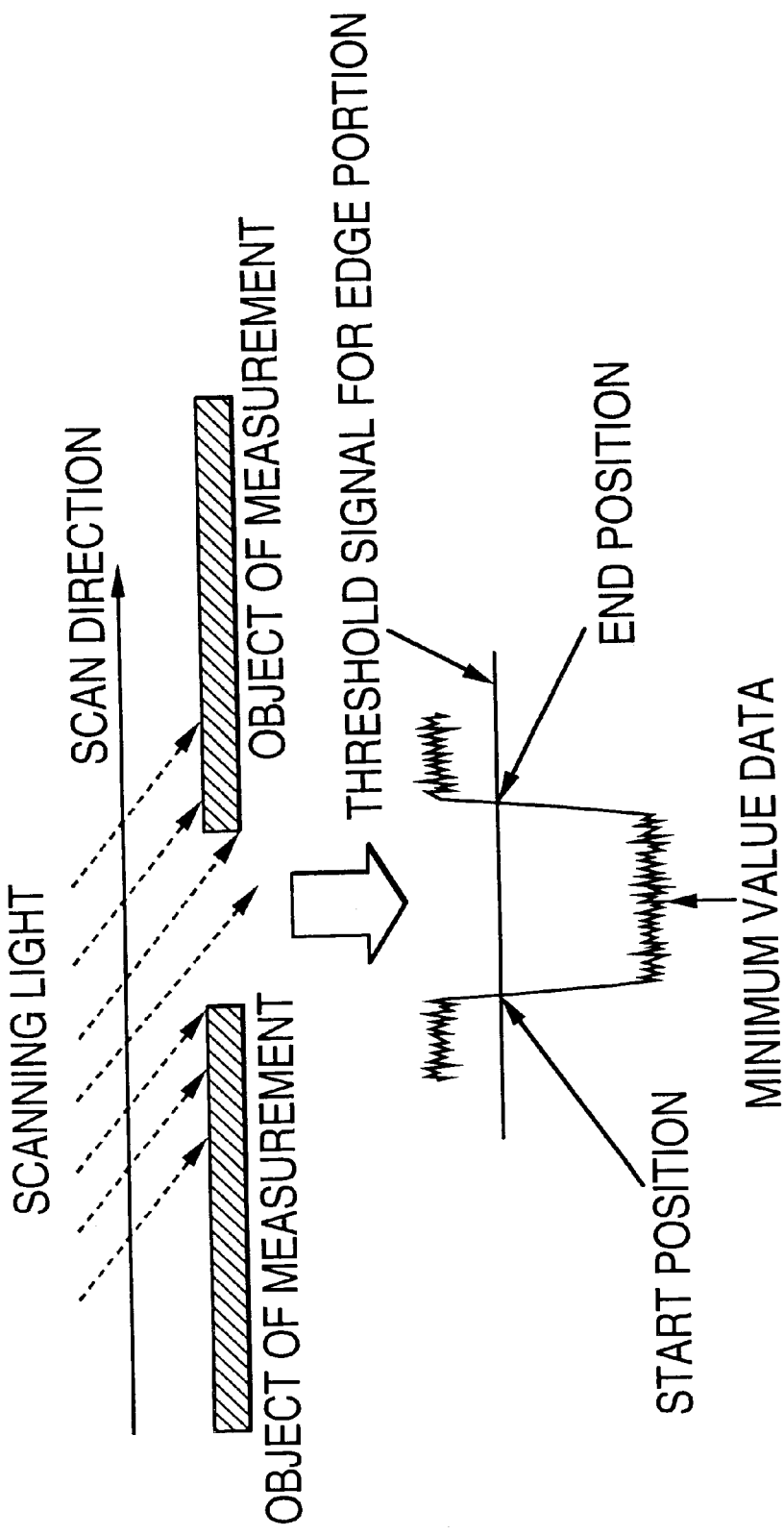
FIG. 14 is a diagram showing a state of measurement in the circumferential range.

The output signal delivered from the edge detecting element when an irradiating light beams in the course of the scan, passes through the cut portion after scanning the object of measurement is shown in FIG. 14.

The minimum value detecting circuit portion sets up such a threshold level for edge detection that makes it possible to distinguish between the reflected light of an irradiating light beam from the irradiating optical system reflected from an object of measurement and an incoming light beam at the time when the reflected light beam from the irradiating optical system stops reflecting because of the object of measurement having an orientation flat. The same, when the signal from the edge detecting element falls below the slice level at a point of time in the course of the scanning, sets the point as the start position, and outputs ENmn start data, the coordinate of the point, Ymn start data corresponding to the displacement of the linear displacement portion 115, and Xmn start data according to the clock signal from the clock circuit CLK as the coordinate data of the point.

The minimum value detecting circuit portion, when, thereafter, the signal from the edge detecting element exceeds the slice level, sets the point as the end position and outputs ENmn end data according to the signal from the encoder, Ymn end data according to the displacement of the linear displacement portion 115, and Xmn end data according to the clock signal from the clock circuit CLK as the coordinate data of the point.

The minimum value detecting circuit portion sets a position between the start position and the end position where the foreign-matter scattered signal was at its minimum as the bottom (depths) and outputs ENmn data according to the signal from the encoder, Ymn data according to the displacement of the linear displacement portion 115, and Xmn data according to the clock signal from the clock circuit CLK as the coordinate values of the position and the bottom level Dmn bottom as the bottom level value.

These coordinate data and the level data are stored in the memory portion through the data processing circuit portion.

Figure 15:
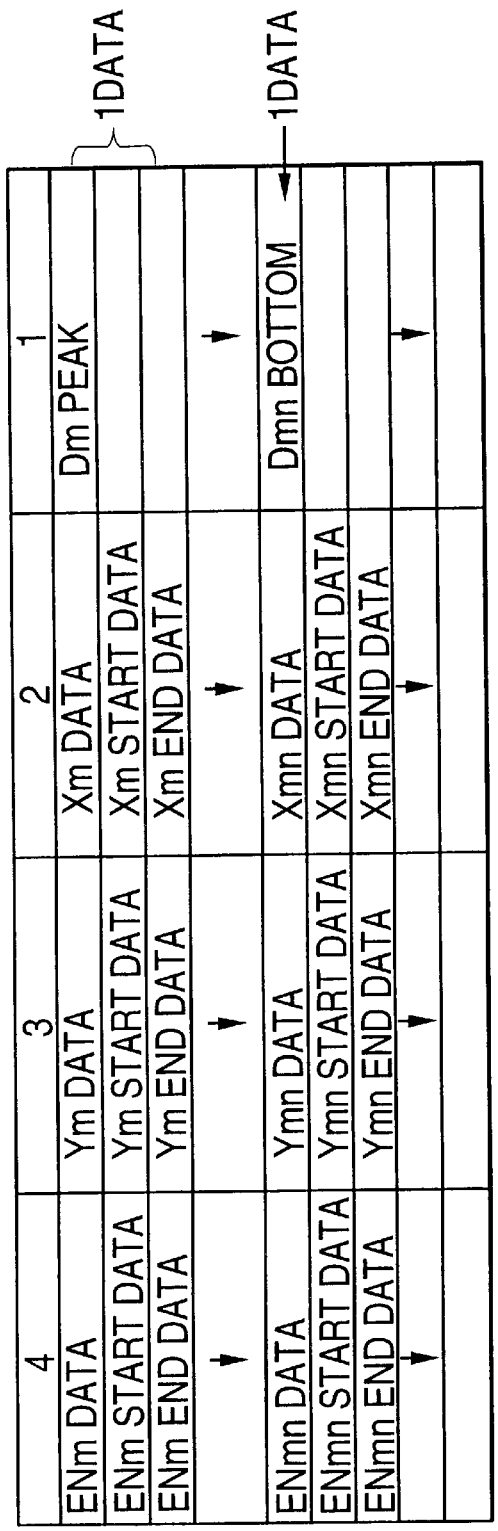
FIG. 15 shows an example of the data memory structure.

The state of the memory address at this time is shown in FIG. 15.

Here, three rows of each column represent one set of measurement data (foreign matter data or orientation flat/notch data).

When the effective range is measured, peak data of a foreign matter is stored in the first row. A peak level, Dm peak, is stored in the first column of the first row, a precise coordinate in the circular direction, Xm data, is stored in the second column of the first row, a coordinate in the radial direction. Ym data, is stored in the third column of the first row, and ENm data, as the coarse coordinate data in the circular direction, is stored in the fourth column of the first row.

Data of the start position of a foreign matter is stored in the second row. Namely, a blank is stored in the first column of the second row, a precise coordinate in the circular direction, Xm start data, is stored in the second column of the second row, a coordinate in the radial direction, Ym start data, is stored in the third column of the second row, and ENm start data, as the coarse coordinate data in the circular direction, is stored in the fourth column of the second row.

Data of the end position of a foreign matter is stored in the third row. Namely, a blank is stored in the first column of the third row, a precise coordinate in the circular direction, Xm end data, is stored in the second column of the third row, a coordinate in the radial direction, Ym end data, is stored in the third column of the third row, and ENm end data, as the coarse coordinate data in the circular direction, is stored in the fourth column of the third row.

When the region of measurement is turned to the circumferential range, data of the bottom come to be stored.

The bottom level, Dmn bottom, of an orientation flat or notch is stored in the first column of the 3n-th row, a precise coordinate in the circular direction, Xmn data, is stored in the second column of the 3n-th row, a coordinate in the radial direction. Ymn data, is stored in the third column of the 3n-th row, and ENmn data, as coarse coordinate data in the circular direction, is stored in the fourth column of the 3n-th row.

Data of the start position of the orientation flat or notch is stored in the (3n+1)-th row. Namely, a blank is stored in the first column of the (3n+1)-th row, a precise coordinate in the circular direction, Xmn start data, is stored in the second column of the (3n+1)-th row, a coordinate in the radial direction, Ymn start data, is stored in the third column of the (3n+1)-th row, and ENmn start data, as coarse coordinate data in the circular direction, is stored in the fourth column of the (3n+1)-th row, In the (3n+2)-th row, there are stored data of the end position of the orientation flat or notch. Namely, a blank is stored in the first column of the (3n+2)-th row, a precise coordinate in the circular direction, Xmn end data, is stored in the second column of the (3n+2)-th row, a coordinate in the radial direction, Ymn end data, is stored in the third column of the (3n+2)-th row, and ENmn end data, as coarse coordinate data in the circular direction, is stored in the fourth column of the (3n+2)-th row.

In either of the effective range and the circumferential range, as described above, a data format made up of a combination of three data, i.e., data of the start position, the end position, and the peak or bottom, is employed. Therefore, by storing the coordinate data in the same way, whether for the effective range or for the circumferential range, in the second column to fourth column, and by storing, only in the first column, the peak level for the effective range or the bottom level for the circumferential range, it in made possible to store data of a foreign matter and data of an orientation flat or notch in the address system of the same form.

Accordingly, the data memory has addresses in the second to fourth columns for common use of the effective range and the circumferential range. Namely, the data memory has at least one arbitrary address for common use and stores data according to the range of measurement.

Further, since such a data form that is made up of the three data of the start position, the end position, and the peak or bottom is adopted, common data processing can be made throughout the effective range and the circumferential range.

Figure 16:
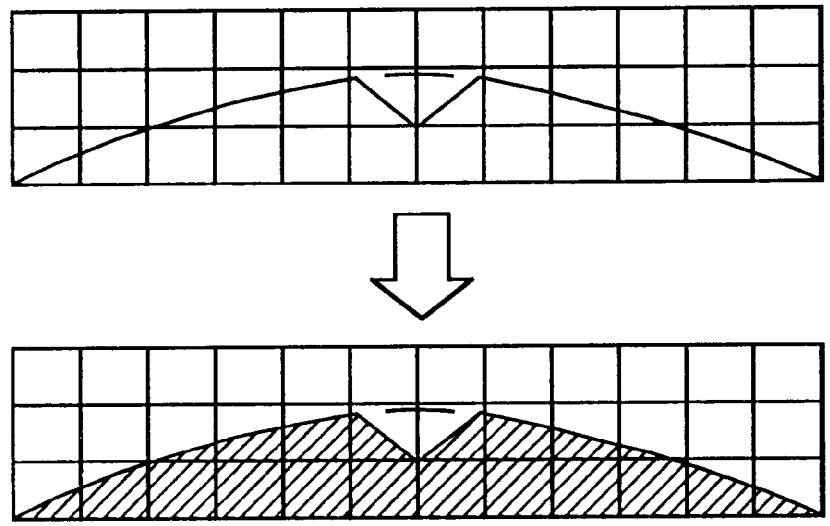
FIG. 16 is a diagram showing a display of the shape of an object of measurement in the circumferential range according to the invention.
Figure 17:
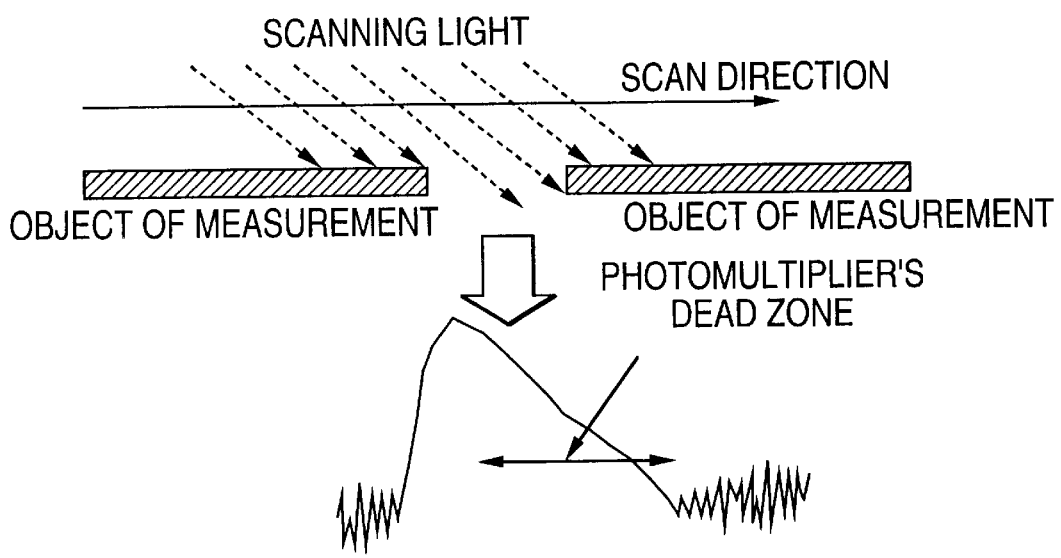
FIG. 17 is a diagram schematically showing a prior art method of surface inspection with the use of a photomultiplier.

The data processing circuit portion can, on the basis of the measurement data indicating the start position coordinates and the end position coordinates stored in the data memory, faithfully reproduce and display on the display portion the shape of a notch in the wafer, corresponding to a cutting in an object of measurement, as shown in FIG. 16.

Thereby, such a problem that a large quantity of scattered light is generated can be prevented from arising not only when the effective range is measured but also when the scanning light comes to scan the circumferential range of the wafer, i.e., when it goes over the effective range into the circumferential range. More specifically, such a trouble can be avoided that the photomultiplier gets saturated in the circumferential range whereby the measurement becomes impossible for a certain period of time.

In the conventional method for surface inspection with the use of a multiplier, because of the problem due to the principle of the multiplier, it was unavoidable that a dead zone is produced by the effect of strong scattered light from the edge portion of the wafer. According to the method for surface inspection of the invention, as apparent from FIG. 6, such a dead zone of the photomultiplier as shown in FIG. 3 is not produced. Even when there is a U notch, V notch, or the like in the wafer, accurate surface inspection can be performed.

As shown in FIG. 16, for example, accurate measurement of the edge can be satisfactorily achieved. Thus, according to the method for surface inspection of the present embodiment, data with coordinates can be recorded even in the measurement of the circumferential range and, therefore, accurate surface inspection of the edge portion can also be achieved.

Below will be described another embodiment of the invention

To the apparatus for surface inspection shown in FIG. 12 is added a second light receiving optical system and an edge detecting element. The second light receiving system is disposed on the extension line of the optical axis of the irradiating optical system 112 so as to receive the light beam passing through a cutting in the circumferential range of the object of measurement. The edge detecting element outputs as its output signal the light beam received by the second light receiving optical system. In this case, since the light beam thrown into the cutting is directly introduced into the second light receiving optical system the output of the edge detecting element becomes high.

Therefore, signal processing is carried out by replacing the minimum value detecting circuit in FIG. 13 with a peak detecting portion or by using the peak detecting portion for the photoelectric converting element also for this detection. As a patter of course, in this variation, processing and storing of the coordinate of the start position, the coordinate of the end position, and the peak data are performed whether in the effective range or in the circumferential range.

Figure 18:
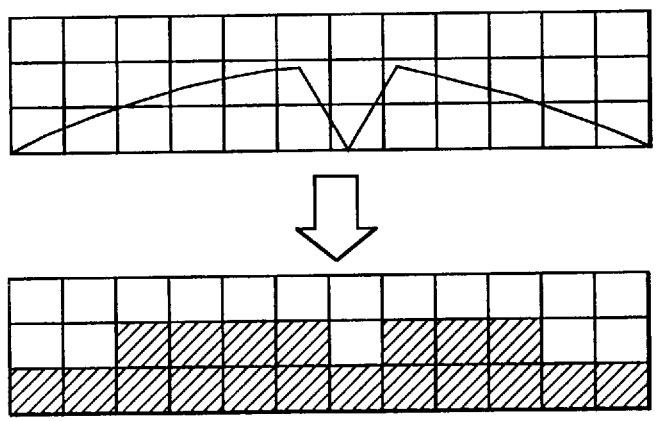
FIG. 18 is a diagram showing a result of surface inspection in a prior art method of surface inspection with the use of a photomultiplier.

The embodiment described with reference to FIG. 18 FIG. 15 has the following meritorious effects:

(1) Data at the edge portion of the wafer can be obtained accurately and the accuracy of the coordinates can be improved.

(2) Since the memory can be used in common, production can be made at low cost.

(3) Resolving powers in the measurement of a foreign matter in the effective range and in the circumferential range can be made different and, therefore, more accurate edge information can be obtained.

(4) By the division of the region of measurement into the effective range which is measured for a foreign matter and the remaining circumferential range, it becomes possible to measure something on the wafer that gives rise to a different sensitivity. For example, when there is a mark of numerals or the like in the circumferential range of a wafer, it may be measured with the same measurement light beam as in the foreign matter inspection and then the character recognition will be made by means of software.

(5) Since the scanning speed and the sampling are variable in any region of measurement, it can be practiced in the circumferential range not only to store representative values but also to store all of the sampled values or only decimated data.

What is claimed is:

1. A method of surface inspection for inspecting a foreign matter on the surface of an object of inspection by throwing an inspecting light beam on the surface of the object of inspection through an optical system and sensing a scattered light beam reflected from the surface of the object of inspection while the object of inspection and the optical system are provided with relative displacement, said method of surface inspection comprising the steps of:

scanning the inspecting light beam on the surface of the object of inspection through the optical system;

sensing a point where the scattered light signal by a foreign matter exceeds a threshold signal or threshold signal level while the inspecting light beam is scanned in a predetermined direction as a start point;

sensing a point where the foreign-matter scattered signal thereafter falls below the threshold signal or threshold signal level as an end point;

sensing a point where the foreign-matter scattered signal was at its maximum level between the start point and the end point as a peak; and evaluating sensed data to determine existence of foreign matter on the surface of the object of inspection.

2. A method of surface inspection according to claim 1, wherein a foreign matter on the surface of an object of inspection is inspected on the basis of positional information, as position data of the foreign-matter scattered signal, including at least a start point, a peak, and an end point.

3. A method of surface inspection according to claim 1, wherein the direction of scan of the inspecting light beam is composed of a scan direction and a feed direction and it is judged that there is continuity in the foreign-matter scattered signal with respect to the feed direction when the positional information including the start point and the end point of a piece of data is overlapping with another piece of data in the feed direction.

4. A method of surface inspection according to claim 1, wherein a stretch from the start point to the end point is considered to be a continuous foreign matter and a process to a the peak data is constantly performed between the start point and the end point.

5. A method of surface inspection according to claim 1 wherein an end point is stored at the point of time at which a piece of data has fallen for the first time below the threshold signal or threshold signal level, counting of the sampling clock is started at the time of point of the end point, and, when the data has risen above the threshold signal or threshold signal level again within preset data, the earlier stored end point is cleared and the process for detecting peak data is continued further.

6. A method of surface inspection according to claim 5, wherein said preset data is variable.

7. A method of surface inspection for inspecting a foreign matter or flaw existing on the surface of an object of measurement comprising the steps of:

scanning the inspecting light beam on the surface of the object of inspection through the optical system;

setting up a threshold signal or threshold signal level between an effective range where a foreign matter or flaw is measured and a circumferential range beyond the effective range;

setting a position where the measurement signal exceeds a threshold signal or threshold signal level while the effective range is being measured as a start position;

setting a position where the measurement signal thereafter exceeds the threshold signal or threshold signal level as an end position; and evaluating the measurement signal and said positions to determine existence of foreign matter on the surface of the object of inspection, wherein a measurement in the circumferential range and a measurement in the effective range are made differently from each other and automatically changed to each other.

8. A method of surface inspection according to claim 7, wherein the quantity of reflected light is stored, while measurement for a foreign matter is being made in the effective range, only when existence of a foreign matter is detected.

9. A method of surface inspection according to claim 8, wherein the data has an arbitrary address for common use.

10. A method of surface inspection according to claim 7, wherein the quantity of reflected light is mainly measured while measurement is being made in the circumferential range and the quantity of reflected light is subjected to a minimum value process.

11. A method of surface inspection according to claim 10, wherein the data has an arbitrary address for common use.

12. A method of surface inspection according to claim 7, wherein any desired sampling manner can be switch selected and the measurement speed is also variable in each of the effective range and the circumferential range.

13. A method of surface inspection according to claim 12, wherein the data has an arbitrary address for common use.

14. A method of surface inspection according to claim 7, wherein, in the effective range where a foreign matter or flaw is measured, maximum values, coordinates, the start position, and the end position regarding data of the foreign matter or flaw are measured.

15. A method of surface inspection according to claim 14, wherein the data has an arbitrary address for common use.

16. A method of surface inspection according to claim 14, wherein the data has an arbitrary address for common use.

17. A method of surface inspection according to claim 7, wherein, in a region of measurement of the circumferential range, minimum values, coordinates, the start position, and the end position in an edge portion of the object of measurement are mainly measured.

18. A method of surface inspection according to claim 17, wherein the data has an arbitrary address for common use.

19. A method of surface inspection according to claim 7, wherein a memory in conformity with the range of measurement is used.

* * * * *